US00PP27692P2

(12) United States Plant Patent
Kobayashi

(10) Patent No.: US PP27,692 P2
(45) Date of Patent: Feb. 21, 2017

(54) **NEW GUINEA *IMPATIENS* PLANT NAMED 'DUESSPROSAUR'**

(50) Latin Name: *Impatiens×hybrida*
Varietal Denomination: Duessprosaur

(71) Applicant: Ruth Kobayashi, Carlsbad, CA (US)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 14/756,455

(22) Filed: Sep. 8, 2015

(51) Int. Cl.
*A01H 5/02* (2006.01)

(52) U.S. Cl.
USPC ..... Plt./318.4

(58) Field of Classification Search
USPC ..... Plt./318.4
CPC ..... A01H 5/0261
See application file for complete search history.

*Primary Examiner* — Kent L Bell
(74) *Attorney, Agent, or Firm* — C. A. Whealy

(57) ABSTRACT

A new and distinct cultivar of *Impatiens* plant named 'Duessprosaur' characterized by its upright, outwardly spreading and mounding plant habit; vigorous growth habit; freely branching habit; dark green-colored leaves; early and freely flowering habit; rose pink-colored flowers; and good garden performance.

1 Drawing Sheet

Botanical designation: *Impatiens×hybrida.*
Cultivar denomination: 'DUESSPROSAUR'.

CROSS-REFERENCED TO CLOSELY RELATED APPLICATIONS

Title: New Guinea *Impatiens* Plant Named 'Duesspneon'Applicant: Ruth Kobayashi Filed: Sep. 8, 2015; concurrently with this application, 14/756,456

BACKGROUND OF THE INVENTION

The present invention relates to a new and distinct cultivar of New Guinea *Impatiens* plant, botanically known as *Impatiens×hybrida* and hereinafter referred to by the name 'Duessprosaur'.

The new *Impatiens* plant is a product of a planned breeding program conducted by the Inventor in Encinitas, Calif. The objective of the breeding program is to create new uniform *Impatiens* plants with numerous attractive flowers and good garden performance.

The new *Impatiens* plant is a naturally-occurring whole plant mutation of a proprietary selection of *Impatiens×hybrida* identified as code number NN-1165-X0000, not patented. The new *Impatiens* plant was discovered and selected by the Inventor as a single flowering plant from within a population of plants of the parent selection in a controlled greenhouse environment in Encinitas, Calif. on Dec. 8, 2014.

Asexual reproduction of the new *Impatiens* plant by terminal vegetative cuttings in a controlled greenhouse environment in Encinitas, Calif. since Jan. 9, 2015 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duessprosaur'. These characteristics in combination distinguish 'Duessprosaur' as a new and distinct *Impatiens* plant:

1. Upright, outwardly spreading and mounding plant habit.
2. Vigorous growth habit.
3. Freely branching habit.
4. Dark green-colored leaves.
5. Early and freely flowering habit.
6. Rose pink-colored flowers.
7. Good garden performance.

Plants of the new *Impatiens* can be compared to plants of the parent selection. Plants of the new *Impatiens* differ primarily from plants of the parent selection in flower color as plants of the parent selection have dark salmon-colored flowers with coral-colored tones.

Plants of the new *Impatiens* can be compared to plants of *Impatiens×hybrida* 'Duesspneon', disclosed in U.S. Plant patent application Ser. No., 14/756,456, filed concurrently. Plants of the new *Impatiens* differ primarily from plants of 'Duesspneon' in flower color as plants of 'Duesspneon' have cerise-colored flowers.

Plants of the new *Impatiens* can be compared to plants of *Impatiens×hybrida* 'SAKIMP012', disclosed in U.S. Plant Pat. No. 19,392. In side-by-side comparisons conducted in Encinitas, Calif., plants of the new *Impatiens* differed primarily from plants of 'SAKIMP012' in the following characteristics:

1. Plants of the new *Impatiens* were more compact than plants of 'SAKIMP012'.
2. Plants of the new *Impatiens* and 'SAKIMP012' differed in flower color as plants of 'SAKIMP012' have red purple-colored flowers with light purple-colored centers.

Plants of the new *Impatiens* can also be compared to plants of *Impatiens×hybrida* 'Misato FG3', disclosed in U.S. Plant Pat. No. 17,662. In side-by-side comparisons conducted in Encinitas, Calif., plants of the new *Impatiens* differed primarily from plants of 'Misato FG3' in the following characteristics:

1. Plants of the new *Impatiens* were more compact than plants of 'Misato FG3'.
2. Plants of the new *Impatiens* and 'Misato FG3' differed in flower color as plants of 'Misato FG3' have magenta-colored flowers.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph at the bottom of the sheet is a side perspective view of a typical flowering plant of 'Duessprosaur' grown in a container.

The photograph at the top of the sheet is a close-up view of a typical flowering plant of 'Duessprosaur'.

DETAILED BOTANICAL DESCRIPTION

The aforementioned photographs and following observations, measurements and values describe plants grown during the summer in 15.25-cm containers in a polyethylene-covered greenhouse in Encinitas, Calif. and under cultural practices typical of commercial New Guinea *Impatiens* production. During the production of the plants, day temperatures ranged from 24° C. to 27° C., night temperatures averaged 18° C. and light levels averaged 4,000 foot-candles. Plants were ten weeks old when the photographs and description were taken. In the following description, color references are made to The Royal Horticultural Society Colour Chart, 2007 Edition, except where general terms of ordinary dictionary significance are used.

Botanical classification: *Impatiens×hybrida* 'Duessprosaur'.

Parentage: Naturally-occurring whole plant mutation of a proprietary selection of *Impatiens×hybrida* identified as code number NN-1165-X0000, not patented.

Propagation:

*Type*.—By terminal cuttings.

*Time to initiate roots, summer and winter*.—About five to seven days at day temperatures about 27° C. and night temperatures about 20° C.

*Time to produce a rooted young plant, summer and winter*.—About three weeks at day temperatures about 27° C. and night temperatures about 20° C.

*Root description*.—Fine, fibrous; white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Upright to outwardly spreading and mounding plant habit; freely branching habit with about ten lateral branches developing per plant; vigorous growth habit.

*Plant height*.—About 18 cm.

*Plant diameter*.—About 35 cm.

Lateral branch description:

*Length*.—About 16 cm.

*Diameter*.—About 9 mm to 12 mm.

*Internode length*.—About 3.2 cm.

*Strength*.—Strong.

*Aspect*.—Initially upright to outwardly spreading.

*Texture*.—Smooth, glabrous.

*Color*.—Close to 187A.

Leaf description:

*Arrangement*.—Opposite or in whorls; simple.

*Length*.—About 9.8 cm.

*Width*.—About 4.4 cm.

*Shape*.—Elliptical.

*Apex*.—Acuminate.

*Base*.—Attenuate.

*Margin*.—Serrulate with ciliation.

*Texture, upper and lower surfaces*.—Smooth, glabrous.

*Luster, upper surface*.—Somewhat glossy.

*Luster, lower surface*.—Matte.

*Venation pattern*.—Pinnate; arcuate.

*Color*.—Developing leaves, upper surface: Close to N137A. Developing leaves, lower surface: Close to 200C. Fully opened leaves, upper surface: Slightly darker than 147A; venation, close to 187C. Fully opened leaves, lower surface: Slightly more grey than 187A; venation, close to 187B.

*Petiole length*.—About 2.4 cm.

*Petiole diameter*.—About 4 mm.

*Petiole texture, upper and lower surfaces*.—Smooth, glabrous.

*Petiole color, upper and lower surfaces*.—Close to 187C.

Flower description:

*Flower type and flowering habit*.—Single rounded and flat axillary flowers; freely flowering habit, typically about 37 flower buds and open flowers per plant at one time; flowers positioned above and beyond the foliar plane, flowers typically face mostly upright to outwardly.

*Flower longevity*.—Flowers typically last about one to two days on the plant under greenhouse conditions; petals self-cleaning, gynoecium persistent.

*Fragrance*.—None detected.

*Natural flowering season*.—Year-round under greenhouse conditions; in the garden, flowering from spring until fall in temperate regions; early flowering habit, plants typically begin flowering about eight weeks after planting.

*Flower buds*.—Length: About 2 cm. Diameter: About 1.3 cm. Shape: Ovoid, pointed. Color: Close to N74B.

*Flower diameter*.—About 4.5 cm by 5 cm.

*Flower depth*.—About 1.4 cm.

*Petals*.—Quantity and arrangement: Five per flower in a single whorl; one upper banner petal, two lateral petals and two lower petals. Length, banner petal: About 2.3 cm. Width, banner petal: About 3 cm. Length, lateral petals: About 2.5 cm. Width, lateral petals: About 2.5 cm. Length, lower petals: About 3.2 cm. Width, lower petals: About 2.7 cm. Shape: Cordate. Apex: Cordate; emarginate. Base: Attenuate. Margin: Entire. Texture, upper and lower surfaces: Smooth, glabrous; velvety. Color: When opening, upper surface: Close to N66A. When opening, lower surface: Close to 72D. Fully opened, upper surface: Close to N66A to N66B; towards the base, close to 71B; central stripes radiating from petal bases, close to 67A; color towards the margins becomes closer to 72B with development. Fully opened, lower surface: Close to 72D; color does not change with development.

*Sepals*.—Quantity and arrangement: Three in a single whorl; one modified into an elongated spur. Length: About 2 cm. Width: About 5 mm. Shape: Narrowly deltoid. Apex: Apiculate. Base: Attenuate. Margin: Entire. Texture, upper and lower surfaces: Smooth, glabrous. Color, upper and lower surfaces: Close to 185C. Spur length: About 5.8 cm. Spur diameter: At the flower, about 3 mm; towards the apex, about 1 mm. Spur texture: Smooth, glabrous. Spur color: Close to 184D.

*Peduncles*.—Length: About 4.2 cm. Diameter: About 2 mm to 3 mm. Angle: About 55° from stem axis. Strength: Strong; flexible. Texture: Smooth, glabrous. Color: Close to 178B.

*Reproductive organs*.—Stamens: Quantity: Five fused at anthers; filaments free. Filament length: Less than 1 mm. Filament color: Close to 1D. Anther size: About 4 mm by 5 mm. Anther shape: Oblong. Anther color: Close to 64A. Pollen amount: Moderate. Pollen color: Close to 158B. Pistils: Quantity per flower: One. Pistil length: About 5 mm. Stigma shape: Rounded. Stigma color: Close to 182D. Style color: Close to 146B. Ovary color: Close to 146B.

*Seeds and fruits*.—Seed and fruit production has not been observed on plants of the new *Impatiens*.

Disease & pest resistance: Plants of the new *Impatiens* have not been observed to be resistant to pathogens and pests common to *Impatiens* plants.

Garden performance: Plants of the new *Impatiens* have been observed to have good garden performance and tolerate temperatures ranging from about 5° C. to about 40° C.

It is claimed:

1. A new and distinct *Impatiens* plant named 'Duessprosaur' as illustrated and described.

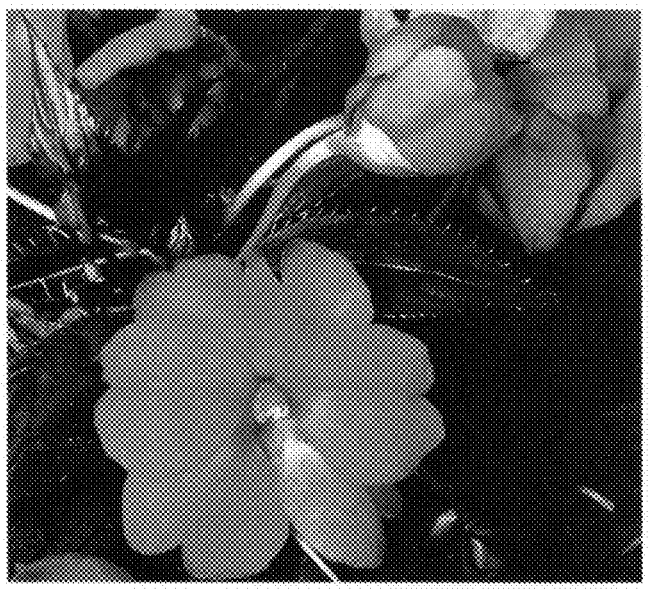
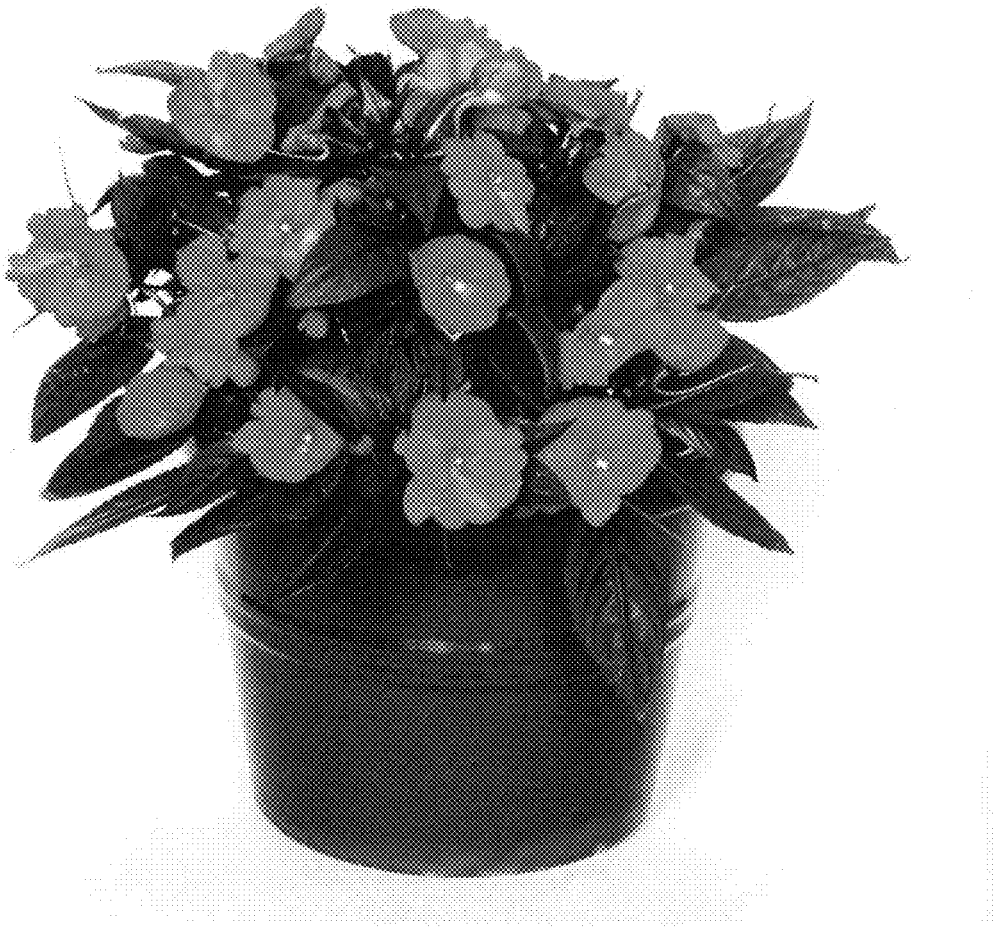

* * * * *